United States Patent [19]

Dutta et al.

[11] Patent Number: 5,546,797
[45] Date of Patent: Aug. 20, 1996

[54] CONSTANT-DEPTH SCRATCH TEST FOR THE QUANTIFICATION OF INTERFACIAL SHEAR STRENGTH AT FILM-SUBSTRATE INTERFACES

[75] Inventors: Indranath Dutta, Marina, Calif.; David P. Lascurain, North Charleston, S.C.

[73] Assignee: The United States of America as represented by the Secretary of the Navy, Washington, D.C.

[21] Appl. No.: 422,725

[22] Filed: Apr. 11, 1995

[51] Int. Cl.$^6$ ........................................ G01N 3/34
[52] U.S. Cl. .................... 73/150 A; 73/81; 73/866
[58] Field of Search ................ 73/866, 838, 841, 73/842, 81, 150 A, 159, 160, 104, 105, 79

[56] References Cited

U.S. PATENT DOCUMENTS

| | | | |
|---|---|---|---|
| 4,606,225 | 8/1986 | Thomason et al. | 73/150 A |
| 4,853,777 | 8/1989 | Hupp | 358/107 |
| 4,856,326 | 8/1989 | Tsukamoto | 73/150 A |
| 4,878,114 | 10/1989 | Huynh et al. | 358/106 |
| 4,934,185 | 6/1990 | Nishiyama et al. | 73/150 A |
| 5,255,562 | 10/1993 | Yamamoto et al. | 73/160 |
| 5,283,642 | 2/1994 | Sarr | 73/105 |

*Primary Examiner*—Richard Chilcot
*Assistant Examiner*—Max Noori
*Attorney, Agent, or Firm*—Donald E. Lincoln; William C. Garvert

[57] ABSTRACT

A Constant-Depth Scratch Test (CDST) technique to quantitatively determine the shear strength of interfaces between thin metallic or non-metallic films and metal or ceramic substrates is revealed. The test overcomes two problems associated with other types of scratch tests, namely the instrumental complexity required for real-time detection of interfacial failure, and the inability to quantify interfacial strength. These problems are circumvented by maintaining a constant depth during scratching through the coating and the substrate, monitoring the horizontal and vertical forces to sustain the constant depth scratch, and finally by using a model to analyze the test results to quantify the interfacial shear strength. Unlike other scratch tests, this test is capable of measuring interfacial shear strength as a function of position on the film-substrate sample.

3 Claims, 8 Drawing Sheets

CONSTANT-DEPTH SCRATCH TEST FOR THE QUANTIFICATION OF INTERFACIAL SHEAR STRENGTH AT FILM-SUBSTRATE INTERFACES

BACKGROUND OF THE INVENTION

1. Field of Invention

This invention pertains to electronic and coating applications. More precisely, this invention involves film-substrate interfaces used in electronic and coating industries. Specifically, this invention reveals a method of maintaining a constant depth during scratch testing and measuring the interfacial adhesion between substrates and films or coatings in micro/opto-electronic and protective/decorative coating applications.

2. Description of the Related Art

Quantitative tests for interfacial adhesion between films and substrates are of critical importance in determining the reliability of components in electronic and coating applications. However, many of the available quantitative tests are applicable only to a limited array of materials systems, or are experimentally complex.

Numerous tests have been proposed in the past to evaluate the quality of interfacial adhesion. Most of the proposed tests yield either qualitative information on interfacial bonding, or quantify the tensile strength of the interface. However, since the vast majority of interfacial failures in both electronic and structural applications occur in shear, it is crucial to quantify the shear strength of interfaces. So far, three different tests have been proposed to accomplish this.

The first test is the peel test reported by Spies in the Journal of Aircraft Engineering, 25 (1953) 64 and by Aravas, et al., in Material Science Engineering, A107 (1989) 159. In that test a fixture is attached to the film to peel the film from the substrate at a fixed angle, the force to do so is measured, and the work of adhesion calculated therefrom. However, the test is restricted to ductile films of greater than ~100 μm thickness which do not break or tear during peeling, and is not applicable to thin, relatively brittle coatings.

The second test is the indentation test reported by Marshall and Evans in the Journal of Applied Physics, 56 (1984) 2632; Rossington, et al., in the Journal of Applied Physics, 56 (1984) 2639; Engel in International Journal of Adhesion and Adhesives, 5 (1984) 455; and Lin, et at., in the Journal of Materials Research 5 (1990) 1110. In that test a loaded indentor is placed on the film attached to the substrate, and the load is incrementally increased until relative lateral displacement between the film and the substrate underneath the indentor causes debonding of the film from the substrate. The critical load for debonding is measured and converted into an interfacial shear strength or fracture toughness. However, that test is somewhat limited in scope, since it requires that the exact applied load at which the interface shears be determined. This is usually accomplished for transparent substrates by using a microscope located below the sample being indented to visually observe debonding, as reported by Lin, et at., in Journal of Materials Research, 5 (1990) 1110. The load for opaque substrates may be determined using acoustic emissions monitoring as reported by Sachsem, et al., in Proceeding MRS Symposium, 154 (1989) 293. However, since large acoustic signals are emitted during indentation due to a number of damage processes, detection of a signal from debonding of the film is usually quite difficult.

The third test which has been proposed to evaluate the quality of interfacial adhesion is a contemporary version of the scratch test, where the film-substrate pair is scratched at a constant speed under a progressively increasing vertical load, as reported by Valli, et al., in Journal of Vacuum Science Technology, A3 (1985) 2411; Julia-Schmutz, et al., in Surface and Coatings Technology, 48 (1991) 1; Wu in Journal of Materials Research, 6 (1991) 407; and Venkataraman, et al., in Thin Solid Films, 223 (1993) 269. In this test, the film eventually detaches from the substrate ahead of the indentor during scratching. The initial debonding event is detected via acoustic emission or from some characteristic of the load-time plot, and the interfacial strength is then determined from the vertical and horizontal loads corresponding to the initial debonding. However, because of the load-controlled nature of the test, significant junction growth (i.e., an increase in the actual area of contact between the microscopic asperities on the surfaces of the indentor and the sample) can occur during scratching, making the indentor ride up and down. This is a special problem for small film thicknesses, since the random variation in scratch depth can be significant in relation to the film thickness, leading to serious limitations associated with mathematical modeling of the process, and hence with the determination of interfacial strength. Additionally, as with the indentation test, there are experimental difficulties associated with the detection of initial interfacial debonding, making the test experimentally complicated and its results hard to interpret.

SUMMARY OF THE INVENTION

The object of the invention disclosed herein is to provide a test method for a constant depth scratch test (CDST) which is conducted under displacement-control, thereby maintaining a constant penetration depth along the length of the scratch. Since the depth of penetration into the film-substrate sample is fixed during scratching, junction growth problems which lead to continuous variations in the actual contact area, and therefore the applied stress, are completely avoided. This prevents the indentor from riding up or down during scratching, making calculation of the horizontal forces required to plough through the film and the substrate during scratching straightforward. This in turn results in a more accurate determination of the force required to shear the film from the substrate, and hence the interfacial shear strength.

A further object of the invention is to provide a test where no complex instrumentation, in terms of in-situ microscopic observations or acoustic emission monitoring, is used to determine the precise moment at which the applied load(s) initially shear(s) the film from the substrate by using a simple apparatus to measure vertical and horizontal forces required to shear the film from the substrate. This is accomplished by having a constant scratch depth, which fixes the geometry of the indentation for the entire length of the scratch, by utilizing indentation theory to calculate the horizontal shear stressed generated at the film-substrate interface due to the vertically applied load for the given geometry, and by using friction and wear theory to calculate the additional horizontal force required to overcome the interfacial shear strength. This combined experimental-cum-theoretical approach completely circumvents the need for sophisticated instrumentation, thus substantially enhancing the user-friendliness of the test, and minimizing the risk of interpretive errors by an operator.

A further object of this invention is to provide the means to calculate the interfacial shear strength between the film and substrate sample at any point on the scratch track; therefore it can be utilized to yield adhesion data as a function of position on the sample. This can be useful when looking at the impact of local effects (such as grain boundaries, secondary phases in substrate, porosity, etc.) on the interfacial shear strength.

Another object of this invention is to provide the means to determine the interfacial shear strength between a wide variety of films and substrates. By appropriate control of the scratch depth, the rate of scratching along the horizontal direction, the indentor shape and size, and corresponding alterations to the theoretical formulas, the test can be adapted to be applicable to a wide range of film and substrate systems. The test can be applied to both ductile and relatively brittle films, which can be as thin as a few thousand angstroms and as thick as a few hundred microns, making the test well-suited to the determination of adhesion of metallizations, conformal coatings or thermal barrier coatings to substrates in both electronic and structural applications.

DESCRIPTION OF THE PREFERRED EMBODIMENT

When an indentor is loaded onto a film attached to a substrate, a shear stress is developed at the film-substrate interface, causing failure if the interfacial shear strength is exceeded. Three types of debond failure can occur, as reported by Lin, et al., in Journal of Materials Research 5 (1990) 1110. For weak interfaces, failure occurs on elastic loading of the film by the indentor (Type I). For intermediate interfacial strength, failure occurs after plastic deformation of the film, but before the indentor penetrates the entire film (Type II). For high interfacial strength, failure occurs after the indentor has penetrated the entire film and plastically deformed the substrate (Type III). For a film substrate system which undergoes Type III debonding, the maximum interfacial shear stress generated at the periphery of a pyramidal shaped indentor (FIG. 1) is given by:

$$\tau_{iv}^{III} = \frac{-0.6875 H_f}{\frac{k'_1(z)}{\phi k_1(z)} + \frac{vt}{b\sqrt{2} \phi^2}} \quad (1)$$

where $H_f$ is the indentation hardness of the film; $v$ is the Poisson's ratio of the film; $t$ is the film thickness; $\phi = [6(1-v)/(4+v)]^{1/2}$; $z = \phi b/t$; $k_1(z)$ is a modified Bessel function of the second kind of the first order; and $k'_1(z)$ is its derivative with respect to $z$.

Figure 1:
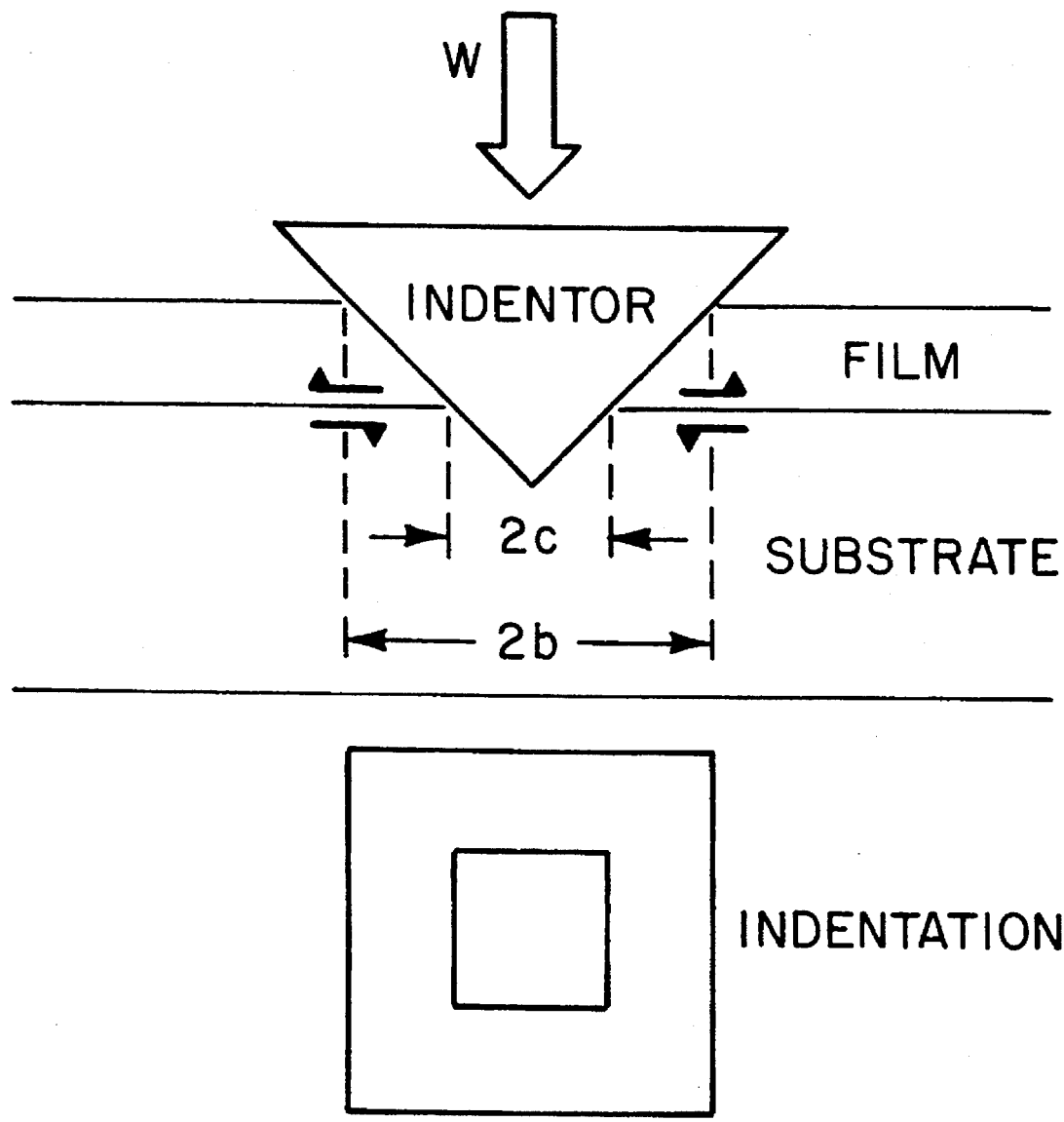
FIG. 1 is a schematic representation of Type III Indentation.

The film hardness, $H_f$, can be shown to be equal to $[(W-4c^2 H_s)/4(b^2-c^2)]$, where $W$ is the applied vertical load; $H_s$ is the indentation hardness of the substrate; and $2b$ and $2c$, as shown in FIG. 1, represent the dimensions of the edges of the square imprints of the pyramidal indentor on the film and the substrate, respectively.

When a film-substrate sample is indented by a pyramidal shaped indentor under increasing vertical load such that the entire film is penetrated, but the indentation is halted prior to the initiation of debonding, the interfacial shear stress due to the vertical load is given in equation 1. The system is now in Type III configuration, although the interface is not debonded. If the indentor is now displaced horizontally relative to the sample, thereby producing a scratch, an additional shear stress ($\tau_{ieff}$) is superimposed on the shear stress already present at the interface due to the vertical force. Together, these two components comprise the total interfacial shear stress.

Figure 2:
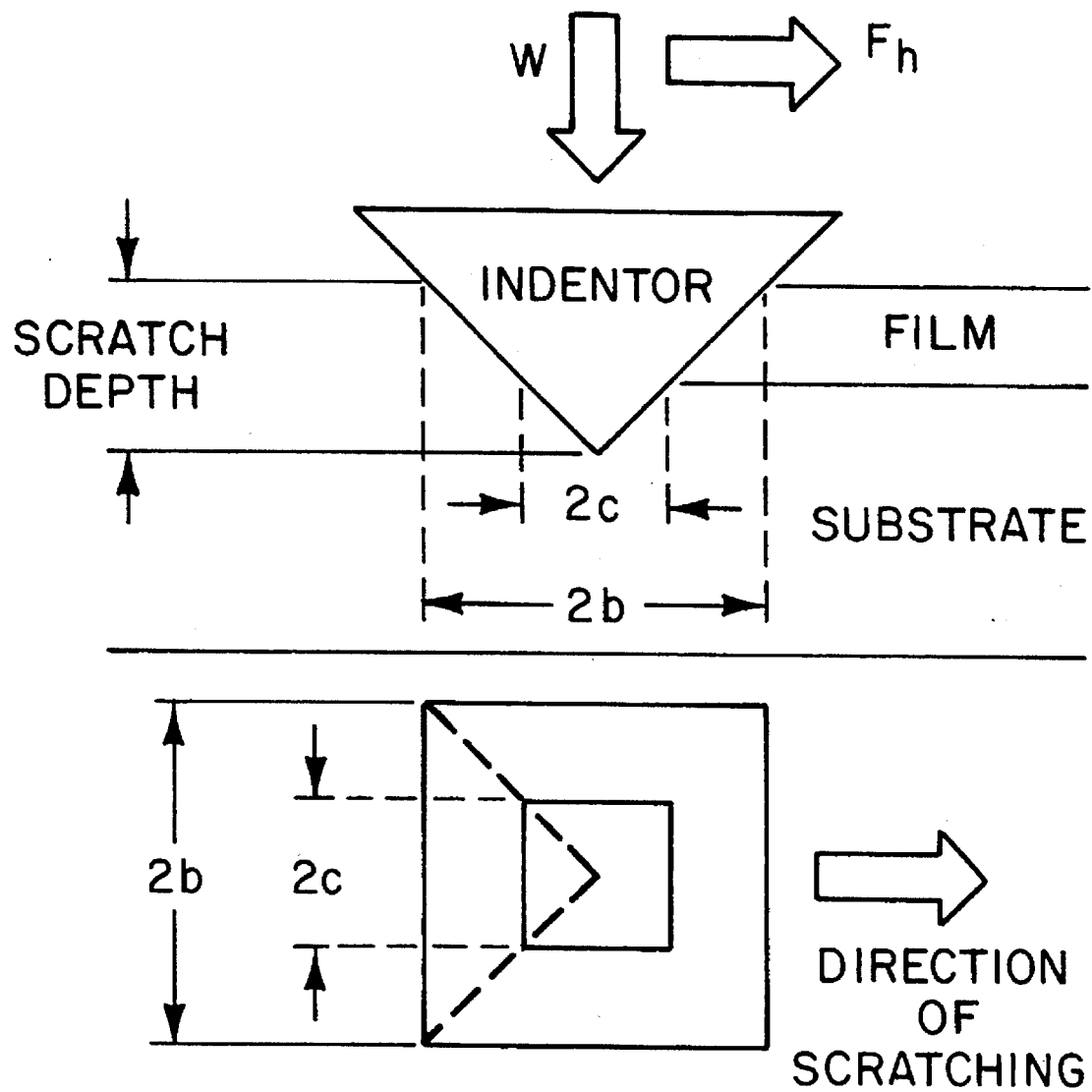
FIG. 2 is a schematic representation of scratch (Type III).

Upon scratching, the shear stress due to the vertical load, given by $$\tau_{iv}^{III}$$

for a stationary indentor, is altered. When a pyramidal indentor is used to scratch the film-substrate sample with a pyramidal face in the forward direction, only three-quarters of the surface area of the indentor is in contact with the test sample (FIG. 2). Therefore $H_f$ equals $[(W-3c^2-H_s)/3(b^2-c^2)]$. Substituting this value in equation 1, the shear stress at the interface due to the vertical force during scratching is:

$$\tau_{ihv}^{III} = \frac{-0.6875 \times \frac{W-3C^2 H_s}{3(b^2-c^2)}}{\frac{k'_1(z)}{\phi k_1(z)} + \frac{vt}{b}\sqrt{2} \phi^2} \quad (2)$$

In addition to the shear stress due to the vertical load during scratching, i.e., $$\tau_{ihv'}^{III}$$

there is an interfacial shear stress, $\tau_{ieff}$, generated due to the applied horizontal force ($F_h$), given by a force balance in the horizontal direction as follows:

$$F_h = F_{s/ind} + P_s + F_{f/ind} P_f + F_{ieff} \quad (3)$$

where $F_{s/ind}$ represents the shear force between the indentor and the substrate; $P_s$ represents the force required to plough through the substrate; $F_{f/ind}$ is the force required for the indentor to shear the film; $P_f$ the force necessary to plough the film; and $F_{ieff}$ is the shear force at the interface due to the applied horizontal force.

$F_{s/ind}$ is given by:

$$F_{s/ind} = S_{s/ind} A_{s/ind} \approx \frac{H_s}{5.5} \times \frac{2c^2}{\sin(\theta/2)} \quad (4)$$

where the substrate shear yield strength $S_{s/ind}$ can be approximated as $(H_s/5.5)$; $A_{s/ind}$ represents the area of contact between the substrate and the indentor along the two side pyramidal faces which shear the substrate; and $\theta$ is the apex angle of the pyramidal indentor.

$P_s$ can be written as:

$$P_s = H_s c^2 \cot(\theta/2) \quad (5)$$

where $c^2 \cot(\theta/2)$ is the area of the leading face on the indentor in contact with the substrate, projected onto a vertical plane normal to the scratch direction.

$F_{f/ind}$ can be written as:

$$F_{f/ind} = S_{f/ind}A_{f/ind} \approx \frac{H_f}{5.5} \times \frac{2(b^2 - c^2)}{\sin(\theta/2)} \quad (6)$$

where $S_{s/ind}$ is the shear yield strength of the film; and $A_{f/ind}$ is the area of contact between the film and the indentor along the two side pyramidal faces.

The film ploughing force $P_f$ is given by:

$$P_f = H_f(b+c)t = \frac{W - 3H_s c^2}{3(b^2 - c^2)} (b+c)t \quad (7)$$

where $(b+c)t$ represents the area of the leading face of the indentor in contact with the film, projected onto a vertical plane normal to the scratch direction.

Since all the quantities on the right hand sides of equations 4 through 7 can be measured, $F_{ieff}$ can be obtained from equation 3 if $F_h$ is known.

$\tau_{ieff}$ can be obtained using $F_{ieff}/4c^2$, where $4c^2$ represents the imprint of the indentor at the film-substrate interface.

The total interfacial shear stress, $\tau_i$, is then given by:

$$\tau_i = \tau_{ihv}^{III} + \tau_{ieff} \quad (8)$$

If the film shears off the substrate during scratching, $\tau_i$ equals the interfacial shear strength.

During scratching of a film-substrate pair, the moving indentor applies a shear stress on the interface ahead of its leading pyramidal face, shears the film and the substrate with the side pyramidal faces, and ploughs through the film and substrate with the leading face. In addition, there may be other damage mechanisms operative, such as flaking, buckling or fracture of the film and/or substrate as reported by Hedenqvist, et al., in Surface and Coatings Technology, 41 (1990) 31 and Bull in Stirface and Coatings Technology, 50 (1991) 25.

Figure 3A:
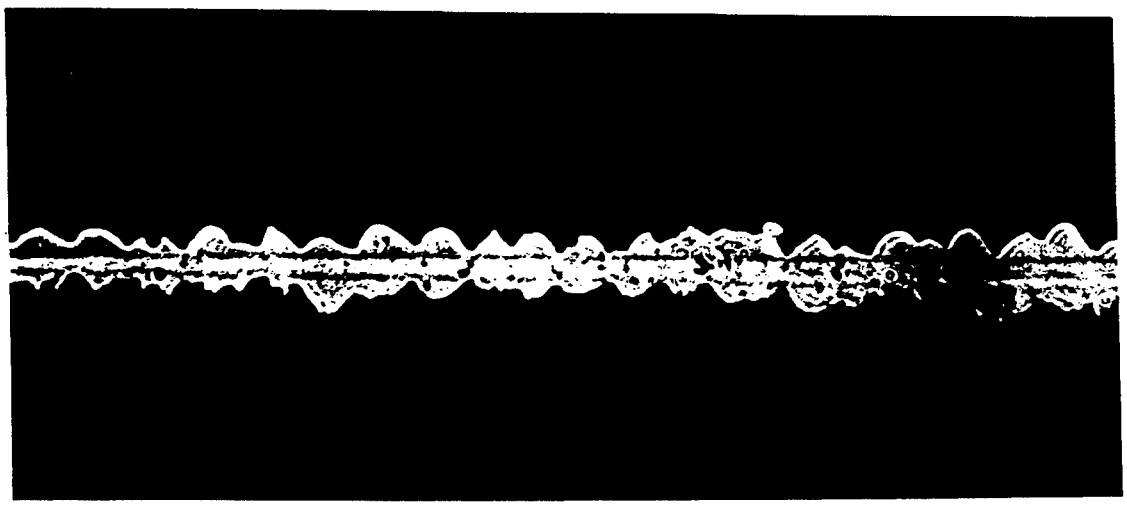
FIG. 3 is the appearance (a) and a model (b) of Forward Lateral Flaking (FLF) during scratching of Chromium on glass.
Figure 3B:
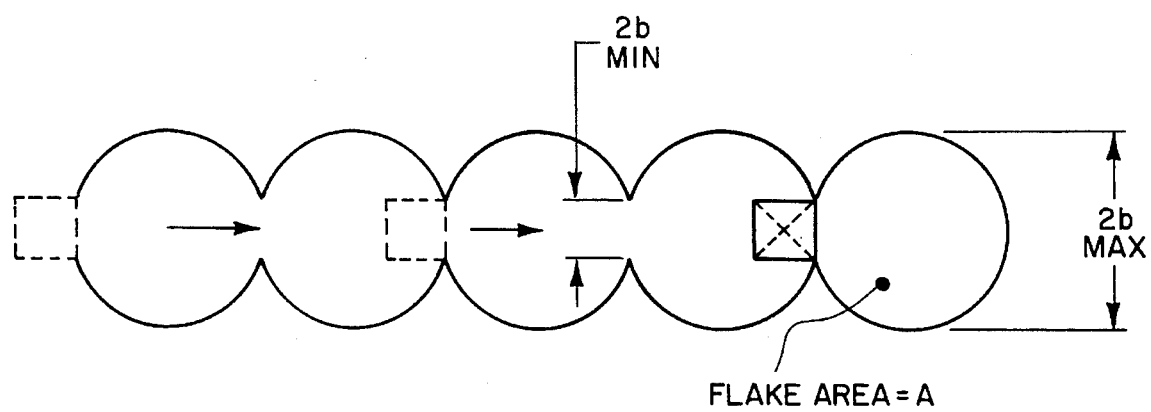

The above derivation of the interfacial shear strength is based on the assumption that no such damage mechanism is operative, and that the indentor cuts through the film-substrate pair cleanly, debonding the film from the substrate as it moves. However, as seen in FIG. 3a, which shows a scratch on a 3650 Å thick Chromium film on glass, the moving indentor typically causes the film ahead of it to flake off from the substrate. This has been referred to as forward lateral flaking (FLF) in the literature (See Hedenqvist, referred to above). In this damage mode, the film gets detached from the substrate in front of the indentor due to the build-up of compressive stresses which cause the film to buckle, resulting in the removal of quasi-circular flakes. Forward lateral flaking (FLF) can be incorporated in the analysis by modeling the scratch as a series of truncated circles, each representing a flake, as shown in FIG. 3b. Accordingly, tile flake area, A, can be approximated as:

$$A = \pi b_{max}^2 - b_{max}^2 \sin^{-1}\frac{b_{min}}{b_{max}} + b_{max}b_{min}\cos\left[\sin^{-1}\frac{b_{min}}{b_{max}}\right] \quad (9)$$

where $2b_{min}$ equals the edge length of the square imprint of the pyramidal indentor on the film; and $2b_{max}$ is the average flake diameter.

In practice, average values of $b_{min}$ and $b_{max}$ can be measured directly by microscopically inspecting the scratch track. To account for shearing of the film off the substrate over the area, A, during FLF, the term $F_{ieff}$ in equation 3 is replaced by:

$$\bar{\tau}_{ieff} A$$

where $$\bar{\tau}_{ieff}$$

is the mean shear stress on the interface under each flake due to $F_h$. Further, since the film flakes off during forward lateral flaking (FLF), it is not sheared by the indentor, necessitating the term $F_{f/ind}$ to be dropped from equation 3. Additionally, tile shear stress due to the vertical load, given by $$\tau_{ihv}^{III}$$

now needs to be averaged over the flake area, A, to yield the mean shear stress $$\bar{\tau}_{ihv}^{III}$$

under the flake due to the vertical force, W. Thus, $$\bar{\tau}_{ihv}^{III} = \frac{1}{A} \int \tau_{ihv}^{III}(r) dA \quad (10)$$

where (r) is the distance of any point under the flake from the center of the indentor, and the interfacial shear strength is given by:

$$\bar{\tau}_i = \bar{\tau}_{ihv}^{III} + \bar{\tau}_{ieff} \quad (11)$$

Figure 4A:
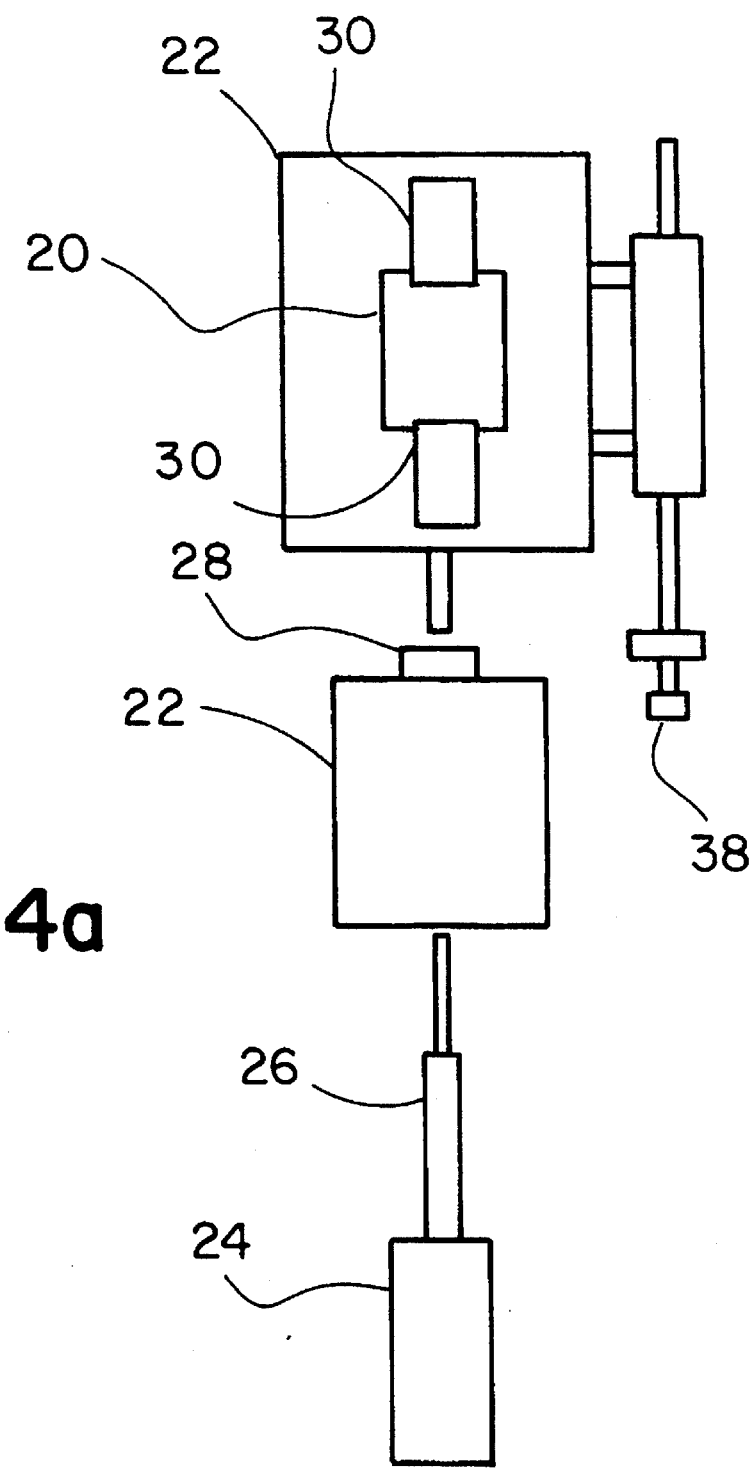
FIG. 4 is a schematic representation of the experimental apparatus.
Figure 4B:
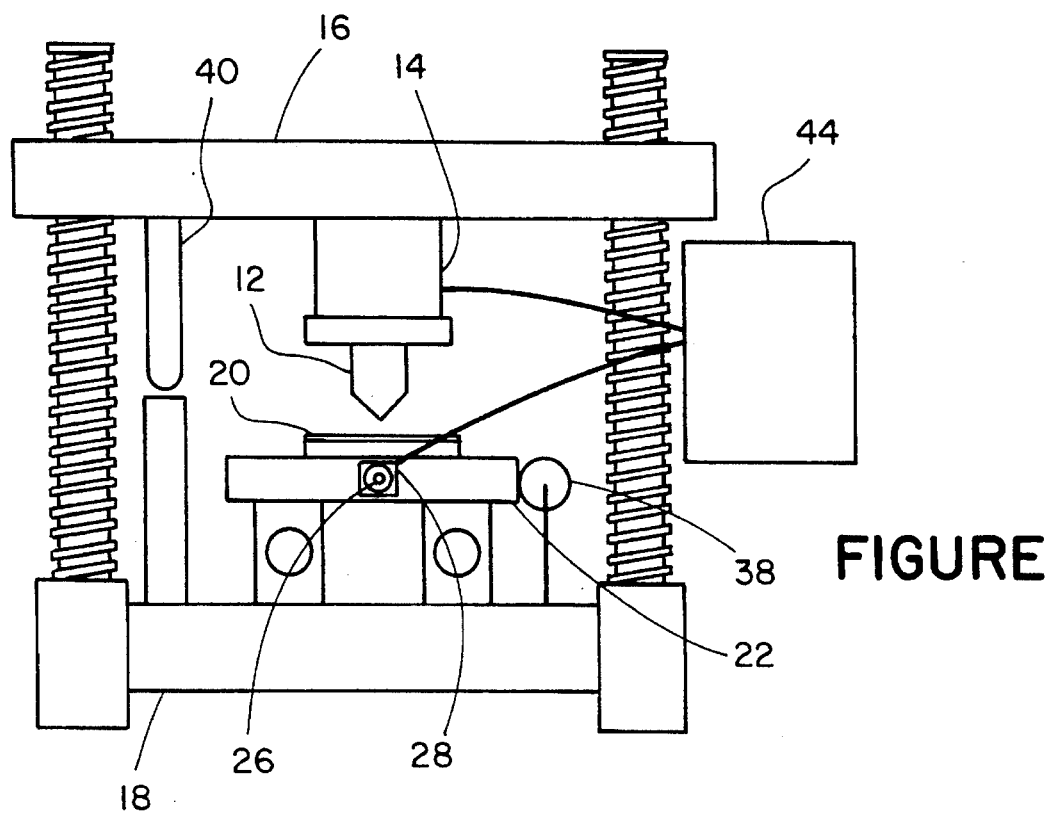

The apparatus (10) for performing the constant depth scratch test is shown schematically in FIG. 4. The set-up consists of a diamond indentor (12), attached to a vertical load cell (14) for measuring the vertical force W, mounted on the moving cross-head (16) of an Instron ™ frame (18). The film-substrate sample (20) is mounted on a motorized translation stage (22), driven by a D.C. Servo-Motor (24). A motorized micrometer drive (26) incorporates a horizontal load cell (28) for measuring the horizontal force $F_h$. The sample (20) is held in place with mounting clips (30). A linear variable displacement transducer, LVDT, (38) is used to measure the horizontal force $F_h$. A micro-proximitor probe (40) is used to measure the initial depth of penetration of the indentor (12) into the sample. The data collected from the vertical load cell (14) and the horizontal load cell (28) are recorded using the Data Acquisition and Analysis System (44), which is also utilized to prepare the data for plotting, and to analyze the input data for the determination of $\tau_i$ as per equations 2 through 11.

EXPERIMENTAL

The film-substrate sample (20) used comprised a number of chromium films of different thicknesses thermally evaporated on silica glass substrates at a base pressure of $5\times10^{-7}$ Torr. Chromium on glass was chosen as the experimental system since preliminary indentation experiments showed that this system undergoes interface failure in Type III (i.e., Cr and glass bond well to each other), so that the model (equations 2–11) developed above is applicable to this system.

Following deposition, each film-substrate sample was indented to various extents by applying a number of different load levels at increments of 5 grams, starting from 0 grams. Each indentation was then inspected under a microscope to determine whether the sample underwent Type II or Type III debonding, and the maximum load at which interface debonding did not occur. The sample was then mounted on the constant-depth scratch tester with the film side up, and indented using this load. Then, keeping the indentation depth constant, the sample was scratched in the horizontal direction, and the corresponding vertical and horizontal forces (W and $F_h$) were measured. To enhance the repeatability of data, a petroleum based lubricant was sprayed onto the sample, as suggested by Valli and Makela in Wear, 115 (1987) 215.

Figure 5A:
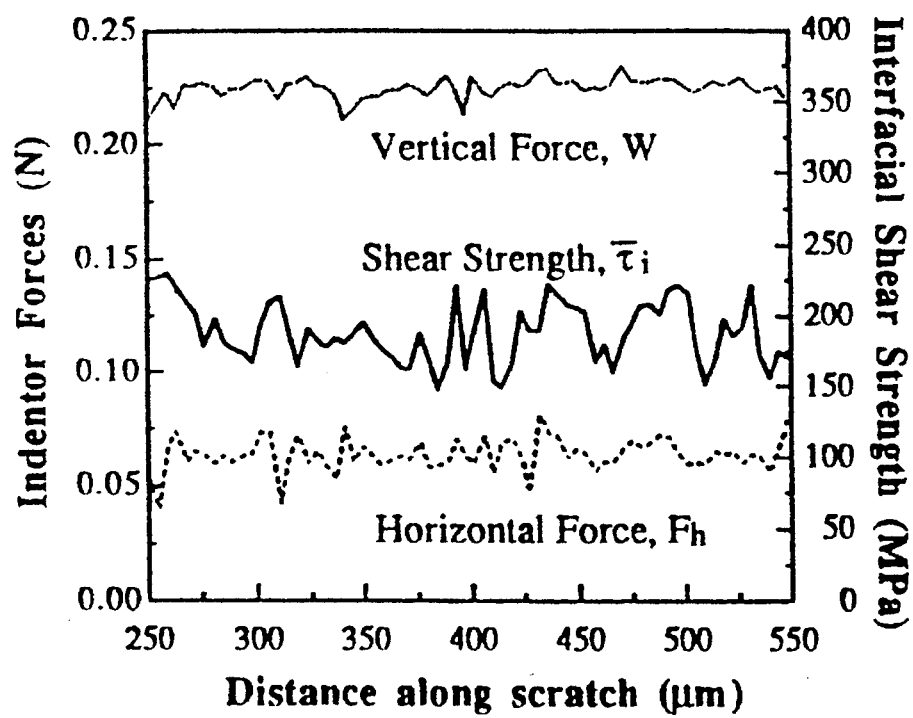
FIG. 5 shows the measured forces and calculated interfacial shear strength for Chromium (Cr) on glass with film thicknesses of (a) 2700 Å and (b) 3300 Å, respectively.
Figure 5B:
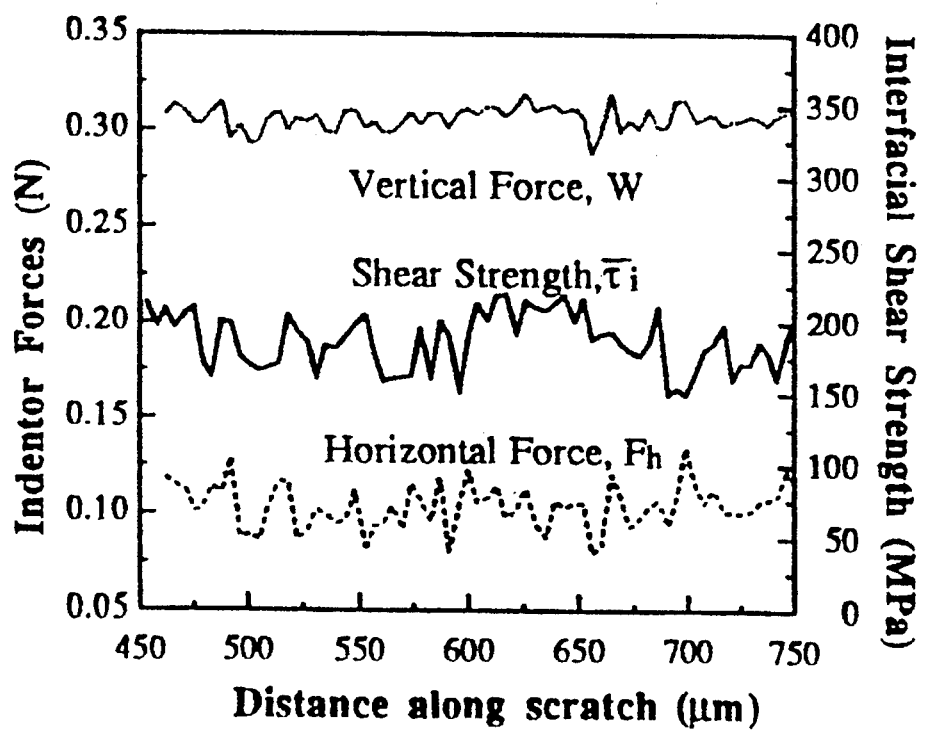

Sample results from the constant depth scratch test are presented in FIGS. 5a and 5b, which show plots of Vertical force, W, and Horizontal force, $F_h$, along with the calculated values of interfacial shear strength as a function of scratch distance for 3300 Å and 2700 Å thick Cr films on glass, respectively. In each experiment, the substrate was penetrated about 0.05 μm. The Vickers hardness of the substrate was 557.7 kg/mm$^2$, and the Poisson's ratio, v, for the film was assumed to be 0.21. As expected, Vertical force, W, and Horizontal force, $F_h$, increase with increasing film thickness, but the calculated shear strength does not appear to display any significant thickness dependence, suggesting that the calculated interfacial shear strength is a good indicator of interfacial adhesion. The sources for the fluctuations in the load traces (and therefore of the shear strength) is not clear, although it is likely to be associated with forward lateral flaking (FLF).

It is to be noted that the values of $b_{max}$ and $b_{min}$ used for the analysis were averages recorded from micrographs of the scratches. Since the actual value of $b_{max}$ is slightly different for each flake, use of the average results in larger fluctuations in the calculated interfacial shear strength than those observed for Vertical force, W, and Horizontal force $F_h$. If a more accurate value of tile interfacial shear strength is desired, $\tau_i$ can be calculated for the interface under each individual flake by utilizing $b_{max}$ and $b_{min}$ values corresponding to that specific flake.

The analytical formulations and tile experimental approach for utilizing a constant depth scratch test (CDST) for measuring the shear strength of film-substrate interfaces has been disclosed, along with preliminary experimental data for Cr-glass interfaces. The constant depth scratch test (CDST) is unique in its ability to measure interfacial shear strength as a function of position on the film-substrate sample to be tested, and simplifies the experimental approach considerably by eliminating the need to discern the initial debonding event.

Through the use of this test, it is possible to alleviate the modeling problems associated with junction growth and the difficulty in detecting the moment of initial debonding by providing a method to quantify the interfacial shear strength between films and substrates. In this approach, a part or the whole of the thickness of the film, which is bonded to the substrate, is indented using a diamond indentor. For strongly bonded interfaces, the whole film thickness is penetrated (Type III indentation), whereas for weakly bonded interfaces, only part of the film thickness is penetrated by the indentor (Type II indentation). The indentor is then displaced relative to the sample to produce a scratch, while maintaining the scratch depth (and hence) geometry constant. During the test, the vertical and horizontal forces (W and $F_h$, respectively) required to sustain scratching are measured. Then, using appropriate theoretical formulations, the shear strength of the film-substrate interface is calculated from the recorded data.

Although forward lateral flaking (FLF) is the only damage mechanism considered to be present during scratching, other mechanisms, if present, can be easily incorporated in the analytical formulations of the test by considering their effect on the horizontal force $F_h$. Further, although the analytical formulation for the constant depth scratch test as disclosed herein is applicable to well-bonded film-substrate samples (i.e., those which undergo Type III bonding), the formulation can be easily extended to relatively weakly bonded interfaces. An approach for this has been discussed by J. C. Campbell in his Master's thesis ["The Measurement of Adhesion at Film-Substrate Interfaces using a Constant Depth Scratch Test", M.S. Thesis, Naval Postgraduate School, December 1994], where he evaluated adhesion of gold-aluminum nitride interfaces.

It will be known by those skilled in the art that this test is quite versatile and is potentially applicable to a wide array of film-substrate systems, including, but not limited to inter-layers, multi-layered, or graded junctions.

Additionally, those skilled in the art will realize that a compact version of the apparatus can be designed fairly easy, making the test suitable for field use in the microelectronics or structural coatings industries. Because of the straightforward experimental approach, the test is not subject to interpretive difficulties like other tests of interfacial adhesion, and all computations can be easily performed in a personal computer connected to the test apparatus, enabling routine use of the test by operators with little training.

It will also be apparent to those skilled in the art that alterations in indentor geometry, the specific mechanism by which a constant scratch depth is maintained during the test, translation of the indentor instead of the sample, and other variations or modifications of the test apparatus and/or the theoretical analyses are all possible variations to this invention of constant-depth scratching.

Obviously, many modifications and variations of the present invention are possible in light of the above teachings. It is, therefore, to be understood that the present invention may be practiced within the scope of the following claims other than as described herein.

What is claimed is:

1. A method of determining the shear strength of film-substrate interfaces, based on precise measurements of the vertical and horizontal loads imposed on a film-substrate sample by an indentor so as to debond the film from the substrate, where the indentation debonding is classified as Type I for weak interfaces when failure occurs on elastic loading of the film by the indentor, and classified as Type II for intermediate interfacial strength when failure occurs after plastic deformation of the film, but before the indentor penetrates the entire film, and classified as Type III for high interfacial strength when failure occurs after the indentor has penetrated the entire film and plastically deformed the substrate, without the necessity of detecting the actual debonding event, comprising the steps of:

causing the indentor to vertically penetrate through the film, partially or completely, depending on whether the film undergoes Type II or Type III indentation debonding, and measuring the vertical force imposed upon the sample;

moving the sample laterally in relation to the indentor, while maintaining the depth of penetration of the indentor into the film constant along the length of the scratch, for measuring the horizontal stress imposed upon the sample by the indentor; and combining the vertical and horizontal force measurements for calculating the inter-facial shear strength of the film-substrate sample as a funcion of position on the sample.

2. A method of scratching a film-substrate sample to determine the shear strength of the interfaces, comprising the steps of:

securing a sample to a test apparatus having a translation stage;

penetrating the film partially or completely with an indentor without debonding the film from the substrate;

displacing the translation stage horizontally to cause the indentor to scratch the substrate, while keeping the depth of penetration of the indentor into the film constant;

measuring the vertical force of the indentor;

measuring the horizontal force of the indentor; and calculating the interfacial shear strength of the film-substrate sample as a function of position on the sample.

3. A method of scratching a film-substrate sample to determine the shear strength of the film-substrate interfaces, based on precise measurements of the vertical and horizontal loads imposed on a film-substrate sample by an indentor so as to debond the film from the substrate, where the indentation debonding is classified as Type I for weak interfaces when failure occurs on elastic loading of the film by the indentor, and classified as Type II for intermediate interfacial strength when failure occurs after plastic deformation of the film, but before the indentor penetrates the entire film, and classified as Type III for high interfacial strength when failure occurs after the indentor has penetrated the entire film and plastically deformed the substrate, without the necessity of detecting the actual debonding event, comprising the steps of:

selecting a film-substrate sample to be tested;

determining whether the sample undergoes Type II or Type III indentation debonding;

placing the sample on a test apparatus;

penetrating the film portion of the sample partially or completely with an indentor while stopping short of debonding the film-substrate interface;

displacing the sample horizontally with a motorized translation stage to cause the indentor to scratch the film while maintaining a constant scratch depth;

recording the vertical force as a function of position on the sample;

recording the horizontal force as a function of position on the sample; and calculating the interfacial shear strength of the film-substrate sample as a function of position on the sample.

* * * * *